United States Patent [19]

Ueda et al.

[11] 4,368,325
[45] Jan. 11, 1983

[54] PROCESSES FOR PREPARING 3-CEPHEM COMPOUNDS

[75] Inventors: Ikuo Ueda, Toyonaka; Masakazu Kobayshi, Ikeda, both of Japan

[73] Assignee: Fujisawa Pharmaceutical Co., Ltd., Osaka, Japan

[21] Appl. No.: 240,469

[22] Filed: Mar. 4, 1981

[30] Foreign Application Priority Data

Mar. 6, 1980 [JP] Japan ................................. 55/29676

[51] Int. Cl.³ .......................................... C07D 501/20
[52] U.S. Cl. ...................................... 544/16; 544/22; 548/194; 562/567
[58] Field of Search ........................... 544/16; 548/194

[56] References Cited

U.S. PATENT DOCUMENTS 4,298,529  11/1981  Ueda et al. ............................ 544/28

Primary Examiner—Paul M. Coughlan, Jr.

Attorney, Agent, or Firm—Oblon, Fisher, Spivak, McClelland & Maier

[57] ABSTRACT

This invention relates to novel compounds of antimicrobial activity of the formula:

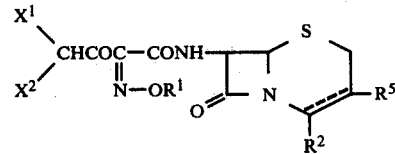

wherein
$R^1$ is an aliphatic hydrocarbon group which may have suitable substituents,
$R^2$ is carboxy or protected carboxy,
$R^5$ is hydrogen or hydroxy,
$X^1$ and $X^2$ are each halogen, and
the dotted line represents cepham or cephem nucleus, or a salt thereof.

7 Claims, No Drawings

PROCESSES FOR PREPARING 3-CEPHEM COMPOUNDS

The present invention relates to a new process for preparing antimicrobially active 3-cephem compounds. More particularly, it relates to a new process for preparing antimicrobially active 3-cephem compounds, to new intermediate compounds which are useful in said process and to processes for the preparation thereof.

Accordingly, it is one object of the present invention to provide a new process for preparing antimicrobially active 3-cephem compounds, e.g. 7-[2-(2-aminothiazol-4-yl)-2-methoxyiminoacetamido]-3-cephem-4-carboxylic acid (syn isomer) or its pharmaceutically acceptable salt.

Another object of the present invention is to provide new intermediate compounds which are useful in said process for preparing antimicrobially active 3-cephem compounds, e.g. 7-[2-(2-aminothiazol-4-yl)-2-methoxyiminoacetamido]-3-cephem-4-carboxylic acid (syn isomer) or its pharmaceutically acceptable salt.

A further object of the present invention is to provide processes for preparing said new intermediate compounds.

The processes included in the present invention are illustrated by the following schemes.

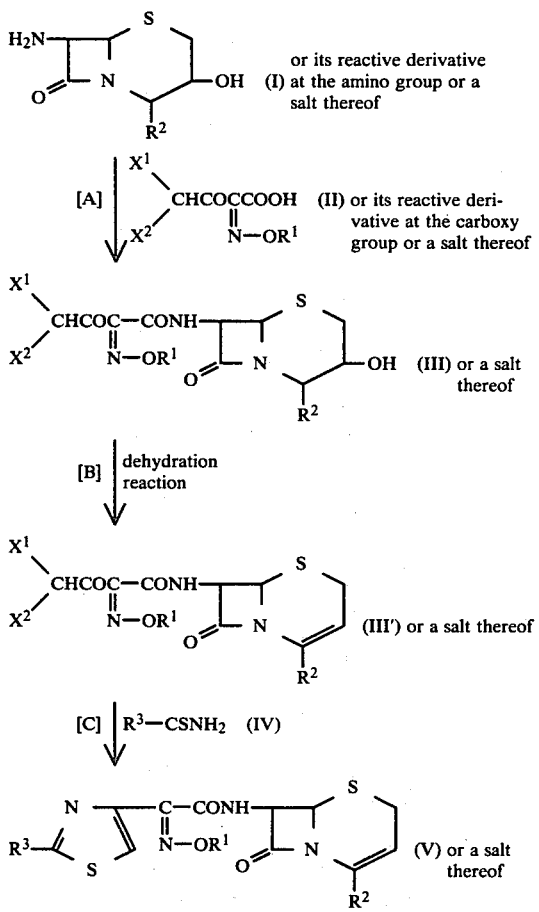

(This compound (V) is disclosed in W. German Offenlegungsschrift No. 2,810,922.)

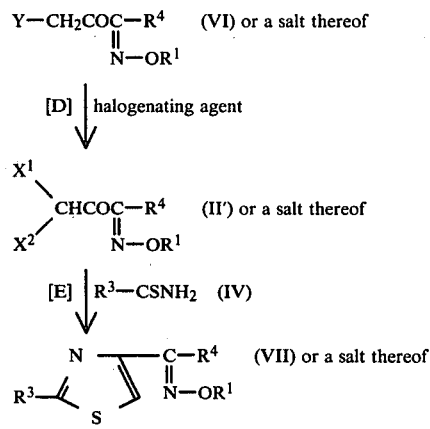

(This compound (VII) is disclosed in W. German Offenlegungsschrift No. 2,810,922.)

wherein
$R^1$ is an aliphatic hydrocarbon group which may have suitable substituent(s),
$R^2$ is carboxy or protected carboxy,
$R^3$ is amino or protected amino,
$R^4$ is carboxy or protected carboxy,
$X^1$ and $X^2$ are each halogen, and
Y is hydrogen or halogen.

Among the compounds of the present invention which are useful as intermediates for preparing the highly active antibiotic compound (V) or a pharmaceutically acceptable salt thereof, preferable new intermediate compounds can be illustrated by the following schemes (i) and (ii) and the compound (III') or a salt thereof per se is also useful as an antibiotic compound.

Scheme (i)

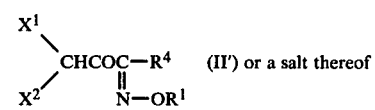

wherein $R^1$, $R^4$, $X^1$ and $X^2$ are each as defined above.

Scheme (ii)

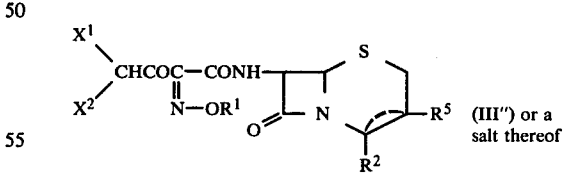

wherein $R^1$, $R^2$, $X^1$ and $X^2$ are each as defined above, $R^5$ is hydrogen or hydroxy, and the dotted line represents cepham or cephem nucleus.

The terms and definitions described in this specification are illustrated as follows.

Partial structure of the formula:

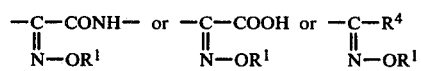

wherein $R^1$ and $R^4$ are each as defined above, is intended to mean the syn isomer.

The term "lower" is used to intend a group having 1 to 6 carbon atoms, unless otherwise provided.

"Protected carboxy" may include an esterified carboxy group.

Suitable examples of "ester moiety" in the "esterified carboxy group" may be lower alkyl ester (e.g. methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g. vinyl ester, allyl ester, etc.);

lower alkynyl ester (e.g. ethynyl ester, propynyl ester, etc.);

lower alkoxy(lower)alkyl ester (e.g. methoxymethyl ester, ethoxymethyl ester, isopropoxymethyl ester, 1-methoxyethyl ester, 1-ethoxyethyl ester, etc.);

lower alkylthio(lower)alkyl ester (e.g. methylthiomethyl ester, ethylthiomethyl ester, ethylthioethyl ester, isopropylthiomethyl ester, etc.);

halo(lower)alkyl ester (e.g. 2-iodoethyl ester, 2,2,2-trichloroethyl ester, etc.);

lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester, etc.);

ar(lower)alkyl, for example, phenyl(lower)alkyl ester which may have one or more suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g. phenyl ester, tolyl ester, t-butylphenyl ester, xylyl ester, mesityl ester, cumenyl ester, salicyl ester, etc.); an ester with a silyl compound such as tri(lower)alkylsilyl compound, di(lower)alkylalkoxysilyl compound or tri(lower)alkoxysilyl compound, for example, tri(lower)alkylsilyl ester (e.g. trimethylsilyl ester, triethylsilyl ester, etc.), di(lower)alkylalkoxysilyl ester (e.g. dimethylmethoxysilyl ester, dimethylethoxysilyl ester, diethylmethoxysilyl ester, etc.) or tri(lower)alkoxysilyl ester (e.g. trimethoxysilyl ester, triethoxysilyl ester, etc.), or the like.

More particularly, the preferable example of ester may be nitrophenyl(lower)alkyl ester (e.g. 4-nitrobenzyl ester, 4-nitrophenethyl ester, etc.), lower alkyl ester (e.g. methyl ester, ethyl ester, propyl ester, isopropyl ester, butyl ester, isobutyl ester, tert-butyl ester, pentyl ester, neopentyl ester, hexyl ester, etc.).

"Protective group" in the "protected amino" may include a conventional amino-protective group such as acyl, substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl may be aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.); and the like.

The acyl as stated above may have 1 to 3 suitable substituent(s) such as halogen (e.g. chlorine, bromine, iodine or fluorine), hydroxy, cyano, nitro, lower alkoxy (e.g. methoxy, ethoxy, propoxy, isopropoxy, etc.), lower alkyl (e.g. methyl, ethyl, propyl, isopropyl, butyl, etc.), lower alkenyl (e.g. vinyl, allyl, etc.), aryl (e.g. phenyl, tolyl, etc.), or the like.

And further, the reaction product of a silan, boron, aluminium or phosphorus compound with the amino group may also be included in the amino-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Aliphatic hydrocarbon group" may include straight or branched alkyl having 1 to 8 carbon atom(s) (e.g. methyl, ethyl, propyl, isopropyl, butyl, isobutyl, t-butyl, pentyl, neopentyl, hexyl, heptyl, octyl, and the like), and more preferably the one having 1 to 4 carbon atom(s), cycloalkyl having 3 to 8 carbon atom(s) (e.g. cyclopropyl, cyclobutyl, cyclopentyl, cyclohexyl, cycloheptyl, cyclooctyl, etc.), or the like, and said aliphatic hydrocarbon group may have suitable substituent(s).

"Halogen" may be chlorine, bromine, iodine or fluorine, and preferred one is chlorine or bromine.

More particularly, the preferable examples of the definitions are illustrated as follows.

The preferable examples of $R^1$ may be lower alkyl (e.g. methyl, ethyl, propyl, isopropyl, butyl, pentyl, etc.), and more preferably the one having 1 to 4 carbon atom(s), and the most preferably methyl.

The preferable example of $R^2$ is carboxy.

The preferable examples of $R^3$ may be amino or acylamino and the most preferably amino.

The preferable examples of $R^4$ is carboxy.

The preferable examples of $X^1$ and $X^2$ may be halogen, and more preferably, bromine or chlorine.

The preferable examples of Y may be hydrogen or halogen (more preferably, bromine or chlorine).

"Salt" may be a pharmaceutically acceptable salt, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like, and these salts can suitably be selected according to the kinds of the compounds of the present invention.

Each process of this invention is explained in detail in the following.

Process [A]

The compound (III) or a salt thereof can be prepared by reacting a compound (I) or its reactive derivative at the amino group or a salt thereof with a compound (II) or its reactive derivative at the carboxy group or a salt thereof.

Suitable reactive derivative at the amino group of the compound (I) may include a conventional reactive derivative as used in a wide variety of amidation reaction, for example, isocyanato, isothiocyanato, a derivative formed by the reaction of a compound (I) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable reactive derivative at the carboxy group of the compound (II) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivative of the compound (I) or (II) can optionally be selected from the above according to the kind of the compound (I) or (II) to be used practically, and other reaction condition.

When the acylating agent (II) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenziosozazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride (i.e. phosphoryl chloride), phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphorus oxychloride (i.e. phosphoryl chloride), phosgene or the like.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction or an optional mixture thereof. The reaction temperature is not critical, and the reaction can preferably be carried out under cooling to warming.

Process [B]

The compound (III') or a salt thereof can be prepared by subjecting the compound (III) or a salt thereof to dehydration reaction.

The dehydration reaction may preferably be conducted by treating a compound (III) or a salt thereof with a dehydrating agent, which may include an organic sulfonic acid such as an alkanesulfonic acid (e.g. methanesulfonic acid, etc.) or an arenesulfonic acid (e.g. p-toluenesulfonic acid, etc.), an organic carboxylic acid such as a halogenated alkanoic acid (e.g. trifluoroacetic acid, etc.); an organic carboxylic acid anhydride (e.g. acetic anhydride, trifluoroacetic anhydride, etc.); a combination of an acid anhydride (e.g. formic acid and acetic anhydride, etc.); an acid halide such as an organic sulfonic halide (e.g. mesyl chloride, tosyl chloride, etc.), an organic carboxylic acid halide (e.g. acetyl chloride, etc.), an inorganic acid halide (e.g. phosphorus oxychloride, thionyl chloride, etc.) and the like.

The dehydration reaction, especially the reaction using an acid halide or acid anhydride type dehydrating agent may preferably be conducted in the presence of a base. The suitable base may be Lewis base such as an organic base (e.g. trimethylamine, triethylamine, N-methylpiperazine, N,N-dimethylaniline, pyridine, anisole, thioanisole, sodium acetate, potassium acetate, etc.), an inorganic base (e.g. sodium hydroxide, potassium hydroxide, ammonium hydroxide, sodium carbonate, potassium carbonate, ammonium carbonate, etc.) and the like.

In case that the acylating agent is used as a dehydrating agent, the hydroxy group of the compound (III) is often acylated by the acylating agent during the reaction. But, thus produced 3-acyloxycepham compound can also be led to the compound (III') by the present reaction without isolation.

The reaction can preferably be conducted in an anhydrous conditions and usually carried out in a conventional solvent such as tetrahydrofuran, dioxane, chloroform, methylene chloride, benzene or any solvent which does not adversely influence the reaction.

The reaction temperature is not critical, and the reaction can preferably be carried out at ambient temperature to under heating.

Process [C]

The compound (V) or a salt thereof can be prepared by reacting the compound (III') or a salt thereof with the compound (IV).

Suitable examples of the compound (IV) may be thiourea, N-(substituted or unsubstituted lower alkanoyl)thiourea (e.g. N-formylthiourea, N-acetylthiourea, N-trifluoroacetylthiourea, etc.), N-(substituted or unsubstituted lower alkoxy carbonyl)thiourea (e.g. N-trichloroethoxycarbonylthiourea, etc.), or the like.

The reaction is usually conducted in a solvent such as water, alcohol (e.g. methanol, ethanol, etc.), benzene, N,N-dimethylformamide, tetrahydrofuran or any other solvent which does not adversely influence the reaction. The reaction temperature is not critical, and the reaction can preferably be carried out at ambient temperature to under heating.

The present reaction can preferably be carried out in the presence of a base such as an inorganic base (e.g. sodium hydroxide, potassium hydroxide, sodium carbonate, potassium carbonate, etc.) or an organic base (e.g. trimethylamine, triethylamine, picoline, N-methylmorpholine, sodium acetate, etc.) and more preferably in the presence of a strong base, wherein a liquid base can be used as a solvent.

Process [D]

The compound (II') or a salt thereof can be prepared by reacting the compound (VI) or a salt thereof with a halogenating agent.

Suitable halogenating agent may include a conventional one which can be used for the halogenation of so-called an activated methylene group, such as halogen (e.g. chlorine, bromine, iodine, etc.), sulfuryl halide (e.g. sulfuryl chloride, sulfuryl bromide, etc.), N-haloimide compound (e.g. N-bromosuccinimide, N-chlorosuccinimide, etc.), a complex of halogen with pyridine (e.g. pyridinium hydrobromide perbromide, etc.), 2-pyrrolidone hydrotribromide, or the like. The reaction can be carried out in the presence of a Lewis acid such as aluminum chloride, boron trifluoride, titanium tetrachloride, and the like. The present reaction is usually conducted in a solvent such as chloroform, methylene chloride, 1,2-dichloroethane, 1,2-dichloropropane, diethyl ether, diisopropyl ether, tetrahydrofuran, dioxane or any other solvent which does not adversely influence the reaction. The reaction temperature is not critical, and the reaction can preferably be carried out at ambient temperature to under heating.

Process [E]

The compound (VII) or a salt thereof can be prepared by reacting the compound (II') or a salt thereof with a compound (IV).

The reaction conditions (i.e. reaction temperature, solvents, etc.) of this reaction may be the substantially same as those illustrated in Process [C].

In order to show the utility of the active compound (V), the test data of the representative compound (V), wherein $R^1$ is methyl, $R^2$ is carboxy, and $R^4$ is amino, i.e. 7-[2-(2-aminothiazol-4-yl)-2-methoxyiminoacetamido]-3-cephem-4-carboxylic acid (syn isomer) are shown in the following.

1. In vitro antibacterial activity:
   (1) Test method:

In vitro antibacterial activity was determined by the two-fold agar-plate dilution method as described below.

One loopful of the 100-fold dilution of an overnight culture of each test strain in Trypticasesoy broth was streaked on heart infusion agar (HI-agar) containing graded concentrations of the test compound and incubated at 37° C. for 20 hours. The minimal inhibitory concentration (MIC) was expressed in µg/ml.

(2) Test results:

| Test Strains | MIC (µg/ml) |
|---|---|
| Staphylococcus aureus 209P JC-1 | 6.25 |
| Escherichia coli. NIHJ JC-2 | ≦0.025 |
| Proteus vulgaris IAM-1025 | ≦0.025 |
| Klebsiella pneumoniae 20 | ≦0.025 |
| Proteus mirabilis 18 | ≦0.025 |
| Pseudomonus aeruginosa NCTC-10490 | 0.39 |
| Serratia marcescens 35 | 1.56 |

The following examples are given only for explaining this invention in more detail.

EXAMPLE 1

Bromine (1.65 g) was added to a solution of 2-methoxyimino-3-oxobutyric acid (syn isomer, 0.5 g) in diethyl ether (5 ml), and the solution was stirred at 50° C. for 3 hours and allowed to stand at room temperature overnight. After washing the resultant solution with 5% aqueous solution of sodium thiosulfate and a saturated aqueous solution of sodium chloride in turn, the solution was dried over anhydrous magnesium sulfate. The solution was treated with the activated charcoal and concentrated under reduced pressure to give oil (1.0 g) of 2-methoxyimino-3-oxo-4,4-dibromobutyric acid (syn isomer).

IR (Nujol): 3700–2100, 1740, 1600, 1040 cm$^{-1}$
NMR (DMSO-d$_6$, δ): 4.12 (3H, s), 7.13 (1H, s)

EXAMPLE 2

Bromine (21.4 g) was added to a solution of 2-methoximino-3-oxo-4-bromobutyric acid (syn isomer, 20 g) in dry diethyl ether (200 ml), and the solution was heated under reflux with stirring for 5 hours. Bromine (4.5 ml) was added to the resultant solution and heated under reflux for 30 minutes. To the resultant solution was added 5% aqueous solution of sodium thiosulfate (80 ml) under ice-cooling and allowed to stand at room temperature overnight. After separating the organic layer, the solution was washed with 5% aqueous solution of sodium thiosulfate (50 ml) and 30% aqueous solution of sodium bromide (50 ml) in turn and dried over anhydrous magnesium sulfate. The solution was treated with activated charcoal and concentrated under reduced pressure to give oil (26 g) of 2-methoxyimino-3-oxo-4,4-dibromobutyric acid (syn isomer).

IR (Nujol): 3700–2100, 1740, 1600, 1040 cm$^{-1}$

NMR (DMSO-d$_6$, δ): 4.12 (3H, s), 7.13 (1H, s)

EXAMPLE 3

Thiourea (377 mg) and sodium acetate (406 mg) were added to a solution of 2-methoxyimino-3-oxo-4,4-dibromobutyric acid (syn isomer, 500 mg) in tetrahydrofuran (5 ml) and water (5 ml), and the solution was stirred at 30° C. for 4 hours. The solution was adjusted to pH 3.5, concentrated under reduced pressure and allowed to stand at 0° C. overnight. The precipitates were collected by filtration, washed with water and dried to give 2-(2-aminothiazol-4-yl)-2-methoxyiminoacetic acid (syn isomer, 135 mg).

IR (Nujol): 3150, 1670, 1610, 1585 cm$^{-1}$

NMR (DMSO-d$_6$, δ): 3.83 (3H, s), 6.85 (1H, s), 7.20 (2H, broad s)

EXAMPLE 4

(1) A solution of 2-methoxyimino-3-oxo-4,4-dibromobutyric acid (syn isomer, 10 g) in methylene chloride (10 ml) was added to a solution of N,N-dimethylformamide (2.89 g) and phosphoryl chloride (6.07 g) in methylene chloride (30 ml) at $-15°$ to $10°$ C., and stirred for an hour. The solution was added to a solution of 7-amino-3-hydroxycepham-4-carboxylic acid (4.8 g) and trimethylsilylacetamide (23.1 g) in methylene chloride (100 ml) at $-15°$ to $-10°$ C., and stirred for 2 hours. To the resultant solution was added water (40 ml) under ice-cooling and stirred for 10 minutes, and then the solvent was removed under reduced pressure therefrom. To the residue was added a saturated aqueous solution of sodium chloride (40 ml) and allowed to stand in a refrigerator overnight. The precipitates were collected by filtration, washed with a saturated aqueous solution of sodium chloride and water in turn, and dried under reduced pressure to give 7-(2-methoxyimino-3-oxo-4,4-dibromobutyramido)-3-hydroxycepham-4-carboxylic acid (syn isomer, 10.27 g).

IR (Nujol): 3450, 3250, 3050, 1760, 1720, 1660, 1580, 1550, 1200, 1180, 1150, 1045, 1000 cm$^{-1}$ NMR (DMSO-d$_6$, δ): 2.6–3.6 (3H, m), 4.13 (3H, s), 4.4 (1H, d, J=7 Hz), 5.15 (1H, d, J=4 Hz), 5.48 (1H, dd, J=4 Hz, 9 Hz), 7.17 (1H, s), 9.53 (1H, d, J=9 Hz)

(2) Acetic anhydride (5 ml), sodium acetate (0.61 g) and potassium acetate (0.73 g) were added a solution of 7-(2-methoxyimino-3-oxo-4,4-dibromobutyramido)-3-hydroxycepham-4-carboxylic acid (syn isomer, 5 g) in dry tetrahydrofuran (50 ml), and stirred at 28° to 29° C. for 4 hours. After hydrogen bromide (5 ml) was added to the resultant solution, tetrahydrofuran was removed under reduced pressure therefrom. To the residue was added water (30 ml) and ethyl acetate (100 ml). The organic layer was separated, washed with water and 30% aqueous solution of sodium bromide in turn, and then dried over anhydrous magnesium sulfate. The solution was treated with activated charcoal, and concentrated under reduced pressure, and then the residue was pulverized with diisopropyl ether. The precipitates were collected by filtration, washed with diisopropyl ether and dried to give 7-(2-methoxyimino-3-oxo-4,4-dibromobutyramido)-3-cephem-4-carboxylic acid (syn isomer, 2.85 g).

IR (Nujol): 3260, 1780, 1700, 1640, 1620, 1580, 1530, 1280, 1220, 1060 cm$^{-1}$ NMR (DMSO-d$_6$, δ): 3.58 (2H, d, J=4 Hz), 4.15 (3H, s), 5.42 (1H, d, J=5 Hz), 5.82 (1H, dd, J=5 Hz, 9 Hz), 6.12 (1H, t, J=4 Hz), 7.1 (1H, s), 9.6 (1H, d, J=9 Hz)

(3) Thiourea (235 mg) and sodium acetate (253 mg) were added to a solution of 7-(2-methoxyimino-3-oxo-4,4-dibromobutyramido)-3-cephem-4-carboxylic acid (syn isomer, 500 mg) in tetrahydrofuran (10 ml) and water (100 ml), and the mixture was stirred at 30° C. for 4 hours. The resultant solution was adjusted to pH 3.5 with 6 N hydrochloric acid, and concentrated under reduced pressure. The precipitates were collected by filtration, washed with water and dried to give 7-[2-(2-aminothiazol-4-yl)-2-methoxyiminoacetamido]-3-cephem-4-carboxylic acid (syn isomer, 163 mg).

IR (Nujol): 3470, 3280, 3200, 1780, 1695, 1655, 1622 cm$^{-1}$

NMR (DMSO-d$_6$, δ): 3.60 (2H, broad s), 3.84 (3H, s), 5.12 (1H, dd, J=5 Hz), 5.84 (1H, dd, J=5 Hz, 8 Hz), 6.52 (1H, broad t), 6.76 (1H, s), 7.26 (2H, broad s), 9.65 (1H, d, J=8 Hz)

What we claim is:

1. A syn compound of the formula:

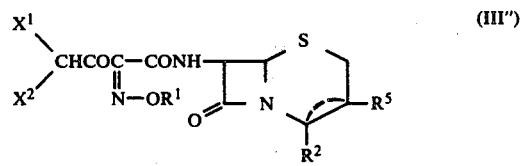

wherein
R$^1$ is an aliphatic hydrocarbon group which may have suitable substituent(s),
R$^2$ is carboxy or protected carboxy,
R$^5$ is hydrogen or hydroxy,
X$^1$ and X$^2$ are each halogen, and
the dotted line represents cepham or cephem nucleus, or a salt thereof.

2. A compound of claim 1,
wherein R$^5$ is hydrogen, and the dotted line represents cephem nucleus.

3. A compound of claim 2,
wherein R$^1$ is lower alkyl, and R$^2$ is carboxy.

4. A compound of claim 3, which is 7-(2-methoxyimino-3-oxo-4,4-dibromobutyramide-3-cephem-4-carboxylic acid (syn isomer).

5. A compound of claim 1,
wherein R$^5$ is hydroxy, and the dotted line represents cepham nucleus.

6. A compound of claim 5,
wherein R$^1$ is lower alkyl, and R$^2$ is carboxy.

7. Compound of claim 6, which is 7-(2-methoxyimino-3-oxo-4,4-dibromobutyramide)-3-hydroxycepham-4-carboxylic acid (syn isomer).

* * * * *